United States Patent [19]

Urdea et al.

[11] Patent Number: 5,594,117

[45] Date of Patent: Jan. 14, 1997

[54] POLYNUCLEOTIDE REAGENTS CONTAINING MODIFIED DEOXYRIBOSE MOIETIES AND ASSOCIATED METHODS OF SYNTHESIS AND USE

[75] Inventors: Michael S. Urdea, Alamo; Thomas Horn, Berkeley, both of Calif.

[73] Assignee: Chiron Corporation, Emeryville, Calif.

[21] Appl. No.: 429,197

[22] Filed: Apr. 26, 1995

Related U.S. Application Data

[63] Continuation of Ser. No. 296,368, Aug. 25, 1994.

[51] Int. Cl.$^6$ .......................... C07H 21/02; C07H 21/04; C07H 19/00; C12Q 1/68
[52] U.S. Cl. ................ 536/23.1; 536/22.1; 536/24.3; 435/6
[58] Field of Search .................... 435/6; 536/24.3, 536/22.1, 23.1

[56] References Cited

U.S. PATENT DOCUMENTS

| | | | |
|---|---|---|---|
| 4,483,964 | 11/1984 | Urdea et al. | 536/25.5 |
| 4,517,338 | 5/1985 | Urdea et al. | 536/25.3 |
| 4,775,619 | 10/1988 | Urdea | 435/6 |
| 4,910,300 | 3/1990 | Urdea et al. | 536/26.8 |
| 5,118,605 | 6/1992 | Urdea | 435/6 |
| 5,256,549 | 10/1993 | Urdea et al. | 435/91.1 |
| 5,359,100 | 10/1994 | Urdea et al. | 522/105 |
| 5,367,066 | 11/1994 | Urdea et al. | 536/24.3 |
| 5,380,833 | 1/1995 | Urdea et al. | 536/22.1 |
| 5,430,136 | 7/1995 | Urdea et al. | 536/24.3 |
| 5,430,138 | 7/1995 | Urdea et al. | 536/26.8 |

FOREIGN PATENT DOCUMENTS

| | | | |
|---|---|---|---|
| 900156 | 8/1991 | Netherlands | C07F 7/18 |
| WO92/02528 | 2/1992 | WIPO | C07H 11/04 |
| WO95/06659 | 3/1995 | WIPO | C07H 21/100 |

OTHER PUBLICATIONS

Azhayeva et al., *Nucleic Acids Research* 23:1170–1176 (1995).
Brandenberg et al., *Bioorg. Med. Chem. Lett.* 5:791–794 (1995).
Chang et al., *Nucleosides & Nucleotides* 10:389–392 (1991).
De Mesmaeker et al., *Synlett* 9:677–679 (1993).
Froehler et al., *Biochemistry* 31:1603–1609 (1992).
Horne et al. *J. Am. Chem. Soc.* 112:2435–2437 (1990).
Hudson et al., *J. Am. Chem. Soc.* 115:2119–2124 (1993).
Kierzek et al., *Nucleic Acids Research* 14:4751–4764 (1986).
Lee et al., *J. Carbohydrate Chemistry* 5:343–357 (1986).
Mahoharan et al., *Tetrahedron Letters* 36:3651–3654 (1995).
von Buren et al., *Tetrahedron* 51:8491–8506 (1995).

*Primary Examiner*—Stephanie W. Zitomer
*Assistant Examiner*—Amy Atzel
*Attorney, Agent, or Firm*—Dianne E. Reed; Kenneth M. Goldman; Robert P. Blackburn

[57] ABSTRACT

Methods and reagents are provided for synthesizing polynucleotides containing modified deoxyribose residues. Monomeric reagents having the structural formula (I)

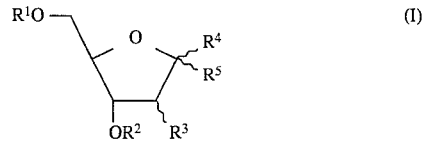

wherein $R^1$, $R^2$, $R^3$, $R^4$ and $R^5$ are as defined herein, are used to create polynucleotides having nonnucleotidic moieties —A—Z—$(R^9)_n$ at the 1 position of selected deoxyribose units. The polynucleotides so provided are useful in a variety of hybridization assay formats.

5 Claims, No Drawings

POLYNUCLEOTIDE REAGENTS CONTAINING MODIFIED DEOXYRIBOSE MOIETIES AND ASSOCIATED METHODS OF SYNTHESIS AND USE

This application is a continuation of application Ser. No. 08/296,368, filed 25 Aug. 1994.

TECHNICAL FIELD

This invention relates generally to nucleic acid chemistry, i.e., DNA synthesis, hybridization assays, and the like, and to reagents used in conjunction therewith. More particularly, the invention relates to methods and monomeric reagents for introducing nonnucleotidic sites—containing modified deoxyribose moieties—into polynucleotides. The invention additionally relates to methods of using the monomeric reagents of the invention and polynucleotide reagents synthesized therefrom in DNA hybridization assays.

BACKGROUND

Nucleic acid hybridization assays are commonly used in genetic research, biomedical research and clinical diagnostics. In a basic nucleic acid hybridization assay, the nucleic acid of interest is hybridized, in single-stranded form, to a labeled single-stranded nucleic acid probe and resulting labeled duplexes are detected. Variations of this basic scheme have been developed to enhance accuracy, facilitate the separation of the duplexes to be detected from extraneous materials, and/or amplify the signal that is detected.

Commonly assigned U.S. patent application Ser. No. 07/559,961, filed Jul. 27, 1990, now U.S. Pat. No. 5,430,136 and incorporated by reference herein, describes a technique whereby selectably cleavable sites are introduced into oligonucleotide chains, enabling release of a detectable label after hybridization is complete. As explained in that application, selectably cleavable sites are useful in a number of different types of hybridization assay formats. For example, in one type of assay in which hybridization gives rise to a solid-supported duplex of a labeled probe and sample DNA, a selectably cleavable site contained within the hybrid structure will enable ready separation of the label from the solid support. Commonly assigned U.S. Pat. Nos. 4,775,619 and 5,118,605 are respectively directed to the use of restriction endonuclease cleavable sites in such assays and the use of chemically cleavable sites (e.g., disulfide linkages, 1,2-diols, and the like). These cleavable sites can be introduced during oligonucleotide synthesis, and are cleavable with restriction endonucleases in the case of restriction sites and with particular chemical reagents, e.g., with thiols, periodate, or the like, in the case of chemically cleavable sites.

The present invention is also directed in part to the incorporation of selectably cleavable sites into polynucleotides. The cleavable sites herein are contained within a linker arm present at the 1 position of a deoxyribose molecule. In addition to providing such cleavable sites, the invention also relates to the creation of "abasic sites" within polynucleotides, i.e., monomeric units which contain the deoxyribose ring but do not have a purine or pyrimidine base present at the 1 position. Such abasic sites are useful in a wide variety of contexts, as will be explained in detail hereinbelow. For example, an abasic site may be used to create branched DNA, i.e., a multimeric polynucleotide structure in which three polynucleotide chains emanate from a single deoxyribose unit. These branch points are extremely useful in providing large, "multimeric" DNA structures which can then be used in amplification assays. Abasic sites may also be used in other ways, e.g., in the synthesis of DNA bound to a solid support (typically although not necessarily at the 1 position), to reverse the direction of chemical DNA synthesis, i.e., 3'→5' to 5'→3' or vice versa, and in triple helix formation.

Thus, in addition to utility in providing cleavable sites within oligonucleotide or polynucleotide chains, the invention enables a number of procedures deriving from the presence of linker arms at the 1 position of a monomeric deoxyribose unit rather than purine or pyrimidine bases as present in conventional nucleotide structures.

OVERVIEW OF THE ART

Background references which relate generally to methods for synthesizing oligonucleotides include those related to 5'-to-3' syntheses based on the use of β-cyanoethyl phosphate protecting groups, e.g., de Napoli et al., *Gazz Chim Ital* 114:65 (1984), Rosenthal et al., *Tetrahedron Letters* 24:1691 (1983), Belagaje and Brush, *Nucleic Acids Research* 10:6295 (1977), in references which describe solution-phase 5'-to-3' syntheses include Hayatsu and Khorana, *J American Chemical Society* 89:3880 (1957), Gait and Sheppard, *Nucleic Acids Research* 4:1135 (1977), Cramer and Koster, *Angew. Chem. Int. Ed. Engl.* 7:473 (1968), and Blackburn et al., *Journal of the Chemical Society*, Part C, 2438 (1967).

In addition to the above-cited art, Matteucci and Caruthers, *J. American Chemical Society* 103:3185–3191 (1981), describe the use of phosphochloridites in the preparation of oligonucleotides. Beaucage and Caruthers, *Tetrahedron Letters* 22:1859–1862 (1981), and U.S. Pat. No. 4,415,732 describe the use of phosphoramidites in the preparation of oligonucleotides. Smith, *ABL* 15–24 (December 1983), describes automated solid-phase oligodeoxyribionucleotide synthesis. See also the references cited therein, and Warner et al., *DNA* 3:401–411 (1984), whose disclosure is incorporated herein by reference.

U.S. Pat. Nos. 4,483,964 and 4,517,338 to Urdea et al. describes a method for synthesizing polynucleotides by selectively introducing reagents to a solid phase substrate in a tubular reaction zone. U.S. Pat. No. 4,910,300 to Horn et al. also describes a method for synthesizing oligonucleotides by sequentially adding nucleotidic monomers to a growing chain, but involves the incorporation of labelled, N-4 modified cytosine residues at predetermined, spaced apart positions. U.S. Pat. No. 5,256,549 to Horn et al. is also of interest in that a method for preparing oligonucleotides is provided which involves a combination technique, i.e., in which the desired oligonucleotide is essentially synthesized and "purified" simultaneously, such that the final product is produced in substantially pure form.

Horn and Urdea, *DNA* 5(5):421–425 (1986), describe phosphorylation of solid-supported DNA fragments using bis(cyanoethoxy)-N,N-diisopropyl-aminophosphine. See also, Horn and Urdea, *Tetrahedron Letters* 27:4705–4708 (1986).

References which relate to hybridization techniques in general include the following: Meinkoth and Wahl, *Anal. Biochemistry* 138:267–284 (1984), provide an excellent review of hybridization techniques. Leary et al., *Proc. Natl. Acad. Sci. (U.S.A.)* 80:4045–4049 (1983) describe the use of biotinylated DNA in conjunction with an avidin-enzyme conjugate for detection of specific oligonucleotide sequences. Ranki et al., *Gene* 21:77–85, describe what they refer to as a "sandwich" hybridization for detection of oligonucleotide sequences. Pfeuffer and Helmrich, *J. Biol. Chem.* 250:867–876 (1975), describe the coupling of guanosine-5'-O-(3-thiotriphosphate) to Sepharose 4B. Bauman et al., *J. Histochem. and Cytochem.* 29:227–237, describe the 3'-labeling of RNA with fluorescers. PCT Application WO 83/02277 describes the addition to DNA fragments of modified ribonucleotides for labeling and methods for analyzing such DNA fragments. Renz and Kurz, *Nucl. Acids. Res.* 12:3435–3444, describe the covalent linking of enzymes to oligonucleotides. Wallace, *DNA Recombinant Technology* (Woo, S., ed.) CRC Press, Boca Raton, Fla., provides a general background of the use of probes in diagnosis. Chou and Merigan, *N. Eng. J. of Med.* 308:921–925, describe the use of a radioisotope-labeled probe for the detection of CMV. Inman, *Methods in Enzymol.* 34B, 24:77–102 (1974), describes procedures for linking to polyacrylamides, while Parikh et al., *Methods in Enzymol.* 34B, 24:77–102 (1974) describe coupling reactions with agarose. Alwine et al., *Proc. Natl. Acad. Sci. (U.S.A.)* 74:5350–5354 (1977), describe a method of transferring oligonucleotides from gels to a solid support for hybridization. Chu et al., *Proc. Natl. Acad. Sci. (U.S.A.)* 11:6513–6529, describe a technique for derivatizing terminal nucleotides. Ho et al., *Biochemistry* 20:64–67 (1981), describe derivatizing terminal nucleotides through phosphate to form esters. Ashley and MacDonald, *Anal. Biochem* 140:95–103 (1984), report a method for preparing probes from a surface-bound template.

Horne and Dervan, *J. Am. Chem. Soc.* 112:2435–2437 (1990), and Froehler et al., *Biochemistry* 31:1603–1609 (1992), relate to oligonucleotide-directed triple helix formation.

SUMMARY OF THE INVENTION

In one aspect of the invention, then, monomeric reagents useful for providing the novel polynucleotide structures are provided, the monomeric reagents having the structural formula (I)

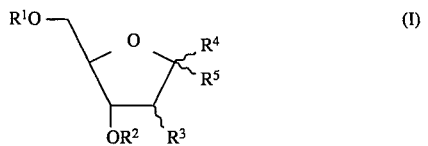

wherein:

$R^1$ is selected from the group consisting of hydrogen, acid-sensitive, base-stable protecting groups and acyl capping groups;

$R^2$ is a phosphorus derivative selected to enable addition of the reagent to a molecular species containing a free hydroxyl group, or is a linkage to a solid support;

$R^3$ is selected from the group consisting of hydrogen, hydroxyl, sulfhydryl, halogeno, amino, alkyl, allyl, —$OR^6$ wherein $R^6$ is alkyl, allyl, silyl or phosphate;

$R^4$ is either hydrogen or —$(CH_2)_mOR^7$ wherein $R^7$ is alkyl or —$(CO)R^8$, $R^8$ is alkyl, and m is an integer in the range of 0 to 12 inclusive;

$R^5$ is —A—Z—X($R^9$)$_n$;

A is oxygen, sulfur or methylene;

Z is arylene, $C_6$–$C_{18}$ aralkylene or $C_1$–$C_{12}$ alkylene containing 0 to 6 heteroatoms selected from the group consisting of O, S, N, Si and Se and 0 to 6 linkages selected from the group consisting of —CO—, —COO—, —CONH—, —NHCO—, —S—S—, —$SO_2$—, —CH(OH)—CH(OH)—, —CH($OR^{15}$)—CH($OR^{15}$)—, —O—PO($O^-$)—O—, —O—PO($R^{15}$)—, —O—PO($OR^{15}$)—O—, —O—PO($OR^{15}$)—$R^{16}$— and —PO($OR^{15}$)—O—$R^{16}$— in which $R^{15}$ is lower alkyl and $R^{16}$ is lower alkylene, and, if Z is aralkylene or alkylene, containing 0 to 3 unsaturated bonds;

X is selected from the group consisting of —NH—, —CONH—, —NHCO—, —CO—, —S— and —Si≡;

$R^9$ is hydrogen, a protecting group, a detectable label, or, unless X is —Si≡, a solid support; and n is 1 when X is —NH—, —CONH—, —NHCO—, —CO—, or —S—, and is 3 when X is —Si≡.

In another aspect, polynucleotide reagents are provided having the structural formulae (II), (III) or (IV)

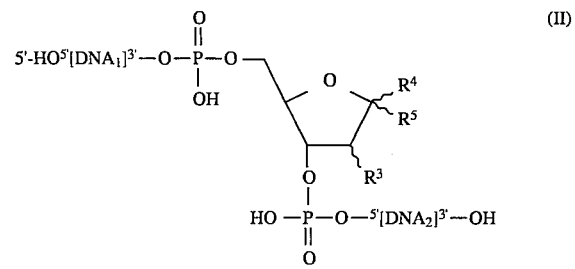

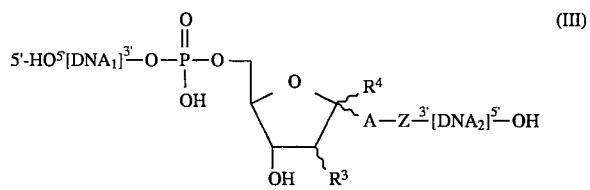

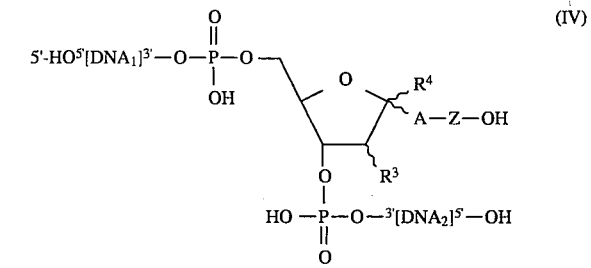

wherein $DNA_1$ represents a first segment of DNA, $DNA_2$ represents a second segment of DNA, and $R^3$, $R^4$ and $R^5$ are as defined above. In a related aspect of the invention, branched DNA is provided having the structural formula (V)

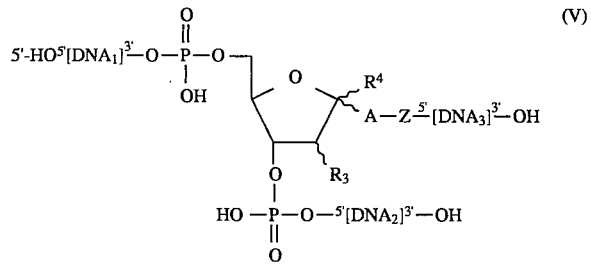

wherein $DNA_1$, $DNA_2$ and $DNA_3$ represent first, second and third segments of DNA, and $R^3$, $R^4$, A and Z are as defined above.

In still other aspects of the invention, methods are provided for synthesizing polynucleotides containing abasic sites and for preparing branched DNA. These methods involve the incorporation of the above-mentioned monomeric reagent into larger polynucleotide structures.

A method is also provided for detecting the presence of an oligonucleotide sequence of interest in a sample which involves hybridizing the nucleic acid sample with a polynucleotide probe containing an abasic site as described herein, wherein the abasic site is formed from the monomeric reagent defined above, and further wherein the reagent contains a detectable label at $R^3$ and a cleavable site within the linker moiety —Z—. Either the sample or the polynucleotide probe is bound to a solid support, such that hybridization results in a label being bound to the support through the cleavable site. Following hybridization, the cleavable site is cleaved with a suitable reagent so as to release the detectable label $R^3$, and label which is free of the support is quantitated and correlated with the presence and/or quantity of sample.

Additionally, probes synthesized using the compounds of the invention may contain 3'-3' linkages, as illustrated in structures (III) and (IV) above. Oligodeoxynucleotide probes containing 3'-3' linkages can be used in triple helix formation, i.e., as such probes can bind to opposite strands of duplex DNA.

DETAILED DESCRIPTION OF THE INVENTION

Definitions and Nomenclature

Before the present invention is disclosed and described in detail, it is to be understood that this invention is not limited to specific assay formats, materials or reagents, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a monomeric reagent" includes mixtures of monomeric reagents, reference to "a polynucleotide probe" may include mixtures of different probes, reference to a polynucleotide containing "an abasic site" includes polynucleotides containing two or more abasic sites, and the like.

In this specification and in the claims which follow, reference will be made to a number of terms which shall be defined to have the following meanings:

As used herein, the terms "polynucleotide" and "oligonucleotide" shall be generic to polydeoxyribonucleotides (containing 2-deoxy-D-ribose), to polyribonucleotides (containing D-ribose), to any other type of polynucleotide which is an N-glycoside of a purine or pyrimidine base, and to other polymers containing nonnucleotidic backbones (e.g., protein nucleic acids and synthetic sequence-specific nucleic acid polymers commercially available from the Anti-Gene Development Group, Corvallis, Oregon, as Neugene™ polymers), providing that the polymers contain nucleobases in a configuration which allows for base pairing and base stacking, such as is found in DNA and RNA. There is no intended distinction in length between the term "polynucleotide" and "oligonucleotide," and these terms will be used interchangeably. These terms refer only to the primary structure of the molecule. Thus, these terms include double- and single-stranded DNA, as well as double- and single-stranded RNA and DNA:RNA hybrids, and also include known types of modifications, for example, labels which are known in the art, methylation, "caps" substitution of one or more of the naturally occurring nucleotides with an analog, internucleotide modifications such as, for example, those with uncharged linkages (e.g., methyl phosphonates, phosphotriesters, phosphoramidates, carbamates, etc.) and with charged linkages (e.g., phosphorothioates, phosphorodithioates, etc.), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

The term "polynucleotide analyte" or "polynucleotide sample" refers to a single- or double-stranded nucleic acid molecule which contains a target nucleotide sequence. The analyte nucleic acids may be from a variety of sources, e.g., biological fluids or solids, food stuffs, environmental materials, etc., and may be prepared for the hybridization analysis by a variety of means, e.g., proteinase K/SDS, chaotropic salts, or the like. The term "polynucleotide analyte" is used interchangeably herein with the terms "analyte," "analyte nucleic acid," "target" and "target molecule." As used herein, the term "target region" or "target nucleotide sequence" refers to a probe binding region contained within the target molecule. The term "target sequence" refers to a sequence with whicha probe will form a stable hybrid under desired conditions.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with halogen, aliphatic groups, or are functionalized as ethers, amines, or the like.

As used herein, the term "probe" refers to a structure comprised of a polynucleotide, as defined above, which contains a nucleic acid sequence complementary to a nucleic acid sequence present in the target molecule. The polynucleotide regions of probes may be composed of DNA, and/or RNA, and/or synthetic nucleotide analogs.

The terms "nucleic acid multimer" or "amplification multimer" are used herein to refer to a linear or branched polymer of the same repeating single-stranded oligonucleotide unit or different single-stranded polynucleotide units, each of which contains a region where a label probe can bind, i.e., contains a nucleic acid sequence complementary to a nucleic acid sequence contained within a label probe; the oligonucleotide units may be composed of RNA, DNA, modified nucleotides or combinations thereof. At least one of the units has a sequence, length, and composition that permits it to bind specifically to a segment of a target polynucleotide; typically, such units will contain approximately 15 to 50, preferably 15 to 30, nucleotides, and will have a GC content in the range of about 20% to about 80%. The total number of oligonucleotide units in the multimer will usually be in the range of about 3 to 1000, more typically in the range of about 10 to 100, and most typically about 50. In one type of branched multimer three or more oligonucleotide units emanate from a point of origin to form a branched structure. The point of origin may be another nucleotide unit or a multifunctional molecule to which at least three units can be covalently bound. In another type, there is an oligonucleotide unit backbone with one or more pendant oligonucleotide units linked to branch points in the backbone. These latter-type multimers are "fork-like," "comb-like" or combination "fork-" and "comb-like" in structure, wherein "comb-like" multimers are polynucleotides having a linear backbone with a multiplicity of sidechains extending from the backbone. Typically, there will be at least two branch points in the multimer, more preferably at least three, more preferably in the range of about 5 to 30, although in some embodiments there may be more. The multimer may include one or more nonnucleotidic segments (e.g., comprised of protein nucleic acids or synthetic sequence-specific nucleic acid polymers, as noted above with respect to "polynucleotides" in general), and one or more segments of double-stranded sequences. Further information concerning multimer synthesis and specific multimer structures may be found in commonly assigned U.S. Pat. No. 5,124,246 to Urdea et al.

As used herein, a "biological sample" refers to a sample of tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). Preferred uses of the present method are in detecting and/or quantitating viral antigens, such as from hepatitis B virus ("HBV"), hepatitis C virus ("HCV"), hepatitis D virus ("HDV"), human immunodeficiency virus ("HIV"), and the herpes family of viruses, including herpes zoster (chicken pox), herpes simplex virus I & II, cytomegalovirus, Epstein-Barr virus, and the recently isolated Herpes VI virus.

By "protecting group" as used herein is meant a species which prevents a segment of a molecule from undergoing a specific. chemical reaction, but which is removable from the molecule following completion of that reaction. This is in contrast to a "capping group," which permanently binds to a segment of a molecule to prevent any further chemical transformation of that segment.

By "abasic site," as noted above, is meant a monomeric unit contained within a polynucleotide chain but which does not contain a purine or pyrimidine base. The term is used interchangeably herein with "modified deoxyribose residue". That is, the monomeric units used in conjunction with the method of the invention contain the deoxyribose ring but do not have a purine or pyrimidine base present at the 1 position.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms, preferably one to four carbon atoms.

The term "alkylene" as used herein refers to a bifunctional saturated branched or unbranched hydrocarbon chain containing from 1 to 24 carbon atoms, and includes, for example, methylene (—CH$_2$—), ethylene (—CH$_2$—CH$_2$—), propylene (—CH$_2$—CH$_2$—CH$_2$—), 2-methylpropylene [—CH$_2$—CH(CH$_3$)—CH$_2$—], hexylene [—(CH$_2$)$_6$—] and the like. "Lower alkylene" refers to an alkylene group of 1 to 6, more preferably 1 to 4, carbon atoms.

The term "aryl" as used herein refers to an aromatic species containing 1 to 5 aromatic rings, either unsubstituted or substituted with 1 or more substituents typically selected from the group consisting of —(CH$_2$)$_x$—NH$_2$, —(CH$_2$)$_x$—COOH, —NO$_2$, halogen and lower alkyl, where x is an integer in the range of 0 to 6 inclusive as outlined above. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically-aryl-substituted alkylene.

The term "arylene" refers to a difunctional aromatic moiety; "monocyclic arylene" refers to a phenylene group. These groups may be substituted with up to four ring substituents as outlined above.

"Optional" or "optionally" means that the subsequently described event or circumstance may or may not occur, and that the description includes instances where said event or circumstance occurs and instances where it does not. For example, the phrase "optionally substituted alkylene" means that an alkylene moiety may or may not be substituted and that the description includes both unsubstituted alkylene and alkylene where there is substitution.

The Monomeric Reagents of the Invention

The monomeric compounds of the invention which are used to create abasic sites within polynucleotide structures have the formula (I)

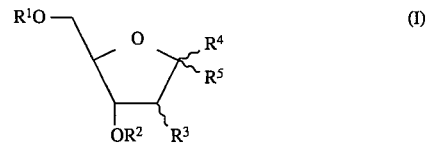

(I)

with R$^1$, R$^2$, R$^3$, R$^4$, R$_5$, A, Z, X and n as defined above It may be seen that reagent (I) is composed of a deoxyribose ring, containing substituents R$^1$ and R$^2$ at the 5 and 3 positions, respectively, which enable incorporation of the reagent into a polynucleotide chain using conventional chemical DNA synthesis techniques. The moiety —A—Z—X(R$^9$)$_n$ at the 1 position replaces the purine or pyrimidine base normally present in a nucleotidic structure, and, as may be deduced from the definition of R$^9$, may be an unprotected moiety, a protected moiety, a labeled moiety, or a linker which is bound to a solid support.

R$^1$ is, as noted above, a base-stable, acid-sensitive blocking group. Such blocking groups are well-known in the art of oligonucleotide synthesis and include unsubstituted or substituted aryl or aralkyl groups, where the aryl is, e.g., phenyl, naphthyl, furanyl, biphenyl, or the like, and where the substituents are from 0 to 3, usually to 0 to 2, and include any noninterfering stable groups, neutral or polar, electron-donating or withdrawing. Examples of such groups are dimethoxytrityl (DMT), monomethoxytrityl (MMT), trityl and pixyl. A particularly preferred moiety for use herein is DMT.

R$^2$ is a phosphorus derivative which is selected so as to facilitate condensation of the reagent with the 5'-hydroxyl group of a nucleoside or an oligonucleotide chain. Such groups include phosphoramidites, phosphotriesters, phosphodiesters, phosphites, H-phosphonates, phosphorothioates, and the like (see, e.g., EP Publication No 0225807 by Urdea et al., "Solution Phase Nucleic Acid Sandwich Assay and Polynucleotide Probes Useful Therein," the disclosure of which is incorporated by reference herein.) Particularly preferred groups useful as $R^2$ are phosphoramidites having the structure:

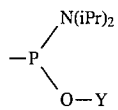

wherein Y is selected from the group consisting of methyl and β-cyanoethyl, and "iPr" represents isopropyl. Most preferably, Y is β-cyanoethyl.

Alternatively, $R^2$ may be a linkage to a solid support, typically through a carbonyl moiety. That is, $R^2$ may be $-(CO)-R^{10}$ wherein $R^{10}$ represents the solid support.

As noted above, the $R^1$ and $R^2$ substituents are generally selected so as to allow incorporation of the monomeric reagent (I) into a DNA fragment using standard phosphoramidite chemistry protocols, well known in the art, and described, for example, in a number of the references cited hereinabove. In general, to incorporate the monomeric reagent (I) into a polynucleotide chain, the $R^2$ substituent is selected so as enable reaction of the reagent at that position (i.e., the 3 position) with the 5'-hydroxyl group of a nucleoside or an oligonucleotide chain, while the $R^1$ moiety is selected so as to enable reaction of the reagent at that position (i.e., the 5 position) with the 3'-hydroxyl of a nucleoside or an oligonucleotide chain.

Examples of preferred monomeric reagents encompassed by structural formula (I) include the following:

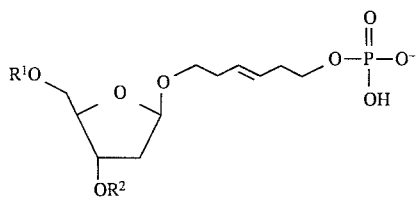

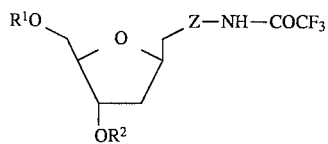

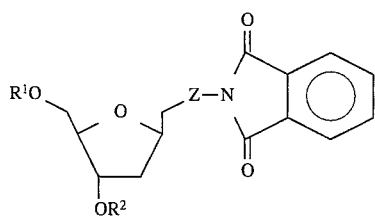

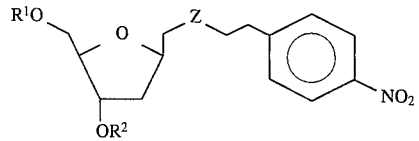

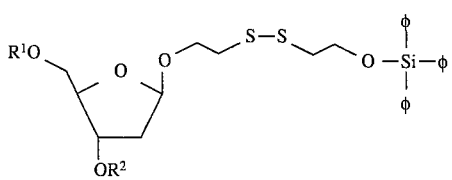

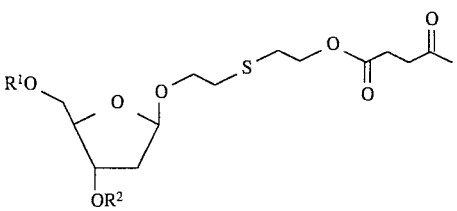

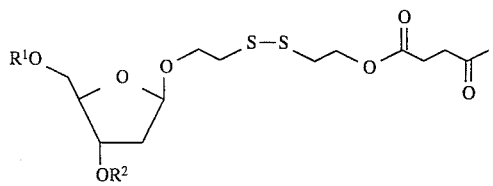

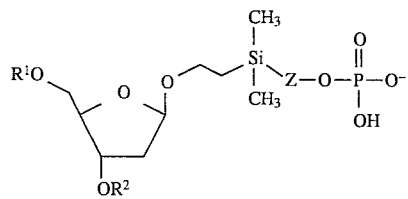

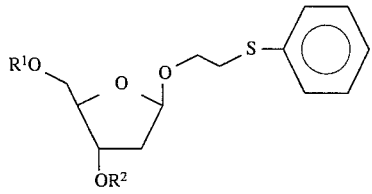

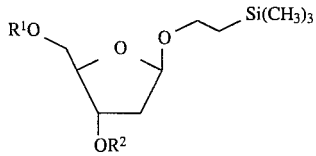

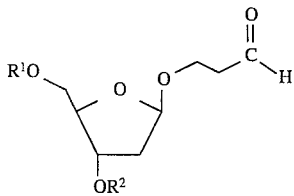

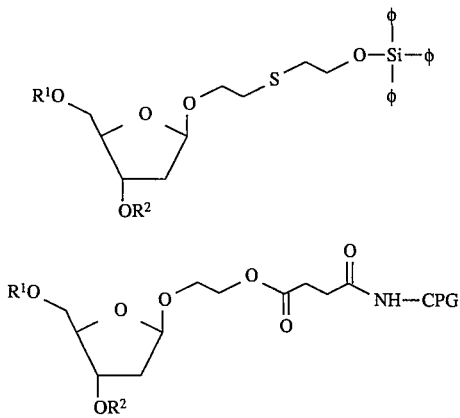
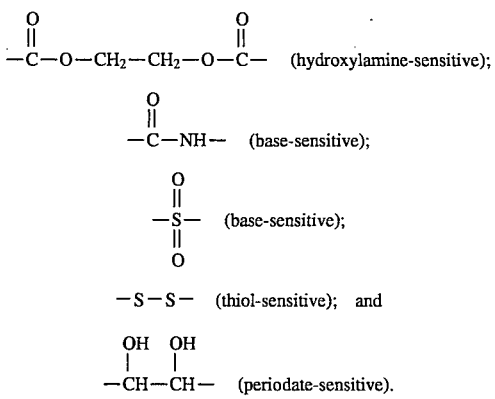

Polynucleotide Reagents Containing Abasic Sites

The polynucleotide reagents of the invention which contain abasic sites are prepared using standard DNA synthesis chemistry and replacing a fraction of the nucleotidic monomers with nonnucleotidic reagent (I). Generally, approximately 1 to 100% of the monomers used to synthesize the polynucleotide reagent will be replaced with reagent (I), more preferably 10 to 50%, and most preferably 20 to 40%. Generally, about 0 to 10 bases will be incorporated between nonnucleotidic monomer units. It is preferred, particularly when the $R^9$ group is a large, bulky substituent, that the nonnucleotidic monomers (I) be spaced apart within the polynucleotide chain. In such a case, at least about 3 bases should be incorporated between monomer units to minimize steric interference or destabilization.

These polynucleotide reagents will generally have the structural formulae (II), (III) or (IV) as shown above.

The polynucleotide reagents of the invention may be used as probes in a wide variety of hybridization assays such as those described in commonly assigned U.S. Pat. Nos. 4,775,619 to Urdea et al., 4,868,105 to Horn et al., 5,118,605 to Urdea, 5,124,246 to Urdea et al., 5,200,314 to Urdea, as well as in PCT Publication Nos. 89/03891 (inventors Urdea et al.) and 92/22671 (inventors Horn et al.). Additionally, with respect to structures (III) and (IV), it should be noted that a 3'-3' linkage is provided, enabling use of the probes in triple helix formation.

In some cases, the linker arm present in nonnucleotidic monomer units resulting from incorporation of reagent (I) into the polynucleotide chain will contain a selectably cleavable site. Probes containing cleavable sites are particularly useful in the hybridization assay described in commonly assigned U.S. Pat. No. 5,118,605 to Urdea et al., entitled "Polynucleotide Determination with Selectable Cleavage Sites," the disclosure of which is incorporated herein by reference. The nature of the cleavable site may vary, but will typically involve a linkage that may be cleaved using readily available chemical reagents, the only limitation here being that the cleavage reagents are compatible with the various probes, labels, etc., used in the remainder of the method. Generally, the cleavable site will be present in the moiety "Z" present within the $R^5$ substituent in the formulae. Preferred cleavable sites are those identified in U.S. Pat. No. 5,118,605. As explained in that application, selectably cleavable sites include, for example, the following types of linkages:

N-hydroxysuccinimide (NHS) may be used to introduce the base-cleavable amide bond into the reagent, while ethylene glycol bis(succinimidyl succinate) may be used to create a hydroxylamine-sensitive linkage, bis[2-succinimidooxycarbonyloxy)ethyl]sulfone (BSOCOES) may be used to create a base-sensitive sulfone linkage, disuccinimidyl tartarate (DST) may be used to introduce 1,2-diols cleavable by periodate, and dithiobis(succinimidylpropionate) (DSP) may be used to provide thiol-cleavable disulfide bonds. Methods of using these reagents to produce the desired cleavable linkage are well known and will be readily apparent to those skilled in the art of synthetic organic chemistry.

In the aforementioned embodiment, the moiety $R^9$ represents a detectable label, such that cleavage of a linkage present within the spacer moiety Z will result in release of label. Suitable labels which may be present at the $R^9$ position in such a case include, for example, radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminl, NADPH, α,β-galactosidase, horseradish peroxidase, and the like.

Polynucleotide reagents useful as probes in hybridization assays may also be prepared by using the monomeric reagent (I) as a "branch point." In this way, probes containing branch points having the structural formula (V)

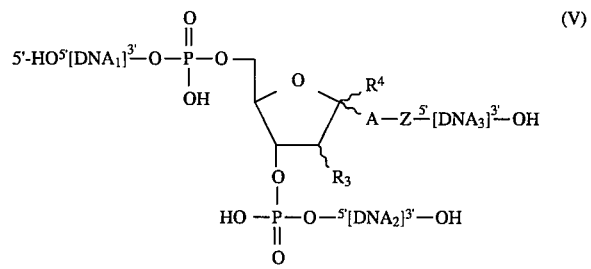

may be prepared wherein $DNA_1$, $DNA_2$, $DNA_3$, $R^3$, $R^4$ and $R^5$ are as defined above. Such probes may be used, for example, in the amplification assays described in commonly assigned U.S. Pat. No. 5,124,246 to Urdea et al., entitled "Nucleic Acid Multimers and Amplified Nucleic Acid Hybridization Assays Using Same," PCT Publication No. WO89/03891, and U.S. patent application Ser. No. 07/813,588. The latter application describes the comb-type branched multimers which are preferred in conjunction with the present method, and which are composed of a linear backbone and pendant sidechains; the backbone includes a segment that provides a specific hybridization site for analyte nucleic acid or nucleic acid bound to the analyte, whereas the pendant sidechains include iterations of a segment that provide specific hybridization sites for a labeled probe.

In still another embodiment of the invention, the "abasic," or modified, site provided by monomeric reagent (I) may be used to enable synthesis of a polynucleotide on a solid support. In this case, the reagent is bound to a solid support through the linker arm at the 1 position, i.e., $R^9$ represents a solid support. As noted above, the linkage to the solid support may also be at the 3 position, at $R^2$. Examples of solid supports include silica, Porasil®C, polystyrene, controlled pore glass (CPG), kieselguhr, poly(dimethylacrylamide), poly(acrylmorpholide), polystyrene grafted onto poly(tetrafluoroethylene), cellulose, Sephadex® LH-20 and Fractosil 500. Nucleotidic monomers are then added using standard DNA synthesis chemistry at the 3' and 5' positions. In some cases, i.e., to produce support-bound labelled probes, it may be desirable to replace some nucleotidic monomers with labelled monomers, e.g., the $N^4$-labelled cytidine derivatives described in commonly assigned U.S. Pat. No. 5,093,232 to Urdea et al., entitled "Nucleic Acid Probes." Such monomers have the structural formula (VI)

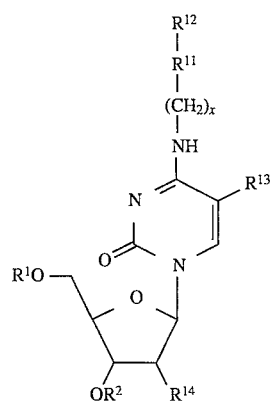

(VI)

wherein $R^1$ and $R^2$ are as defined above;

$R^{11}$ is an optional linking moiety which, if present, contains an amide, thioether or disulfide linkage or a combination thereof;

$R^{12}$ is a reactive group derivatizable with a detectable label, e.g., —$NH_2$, —COOH or —SH;

$R^{13}$ is hydrogen, methyl, fluoro, bromo or iodo; and $R^{14}$ is either hydrogen, hydroxyl or protected hydroxyl.

In still another embodiment of the invention, polynucleotides are synthesized in which the monomeric reagent (I) may be used to change the direction of synthesis, e.g., from 3'→5' to 5'→3' or vice versa. This is accomplished by adding monomeric reagent (I) to the terminus of a growing oligonucleotide chain, capping either the 3' or 5' terminal hydroxyl group with a capping group, typically an acyl capping group, and then using the 1 linker arm to continue synthesis in the reverse direction. Oligomers in which adjacent monomer units are linked 3'-3' can also be prepared using reagent (I), by binding the oligonucleotide to a solid support at $R^9$, growing a single oligomer at the 5' position, capping exposed the exposed hydroxyl group at the 5' terminus, and then growing a second oligomer at the 3' position. Such structures are illustrated in formulae (II) and (III).

Synthetic Methods

Scheme I illustrates the preferred method of synthesizing monomeric reagents having the structural formula (I):

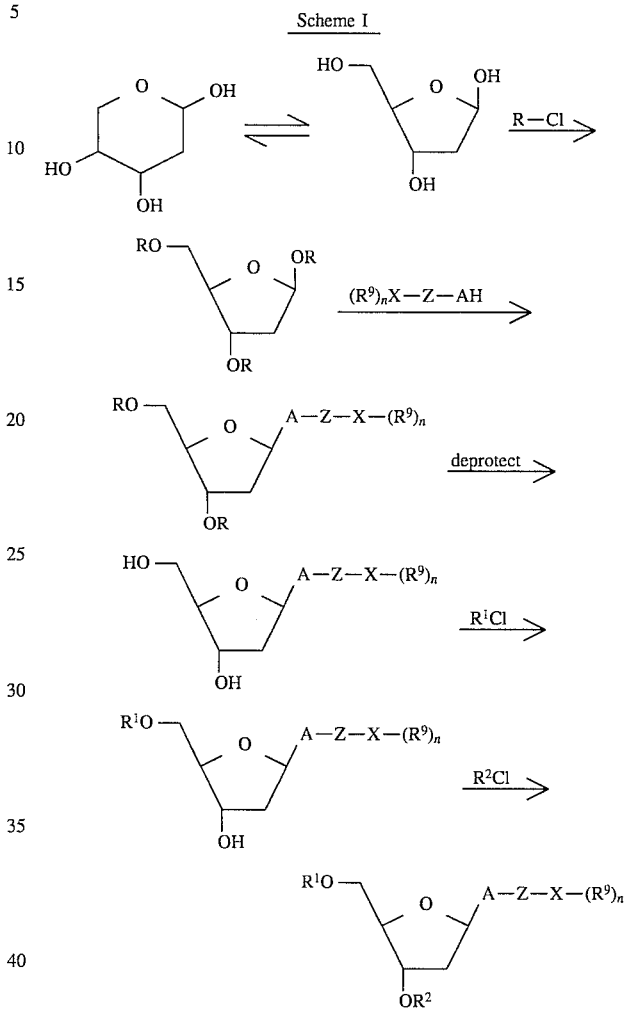

In Scheme I, 2-deoxy-D-ribofuranose is used as the starting material. The three hydroxyl groups of the molecule are protected using an "R-Cl" reagent or some other reagent suitable to protect free hydroxyl groups (e.g., benzoyl chloride or acetic anhydride) to provide 3 —OR groups at the 1, 3 and 5 positions of the sugar. The product is isolated, and the 1-OR group then replaced by reaction with a moiety $(R^9)_n$—X—Z—AH in the presence of an acid catalyst, followed by deprotection at the 3 and 5 positions using base. The 5 position may then be selectively protected by reaction with $R^1$-Cl, e.g., dimethoxytrityl chloride, followed by reaction with a selected phosphoramidite at the 3 position to provide the desired phosphorus derivative.

Experimental

The practice of the present invention will employ, unless otherwise indicated, conventional techniques of synthetic organic chemistry, biochemistry, molecular biology, and the like, which are within the skill of the art. Such techniques are explained fully in the literature. See, e.g., Sambrook, Fritsch & Maniatis, *Molecular Cloning: A Laboratory Manual*, Second Edition (1989); *Oligonucleotide Synthesis* (M. J. Gait, ed., 1984); *Nucleic Acid Hybridization* (B. D. Hames & S. J. Higgins, eds., 1984); and a series, *Methods in Enzymology* (Academic Press, Inc.). All patents, patent applications, and publications mentioned herein, both supra and infra, are hereby incorporated by reference.

It is to be understood that while the invention has been described in conjunction with the preferred specific embodiments thereof, that the description above as well as the example which follows are intended to illustrate and not limit the scope of the invention. Other aspects, advantages and modifications within the scope of the invention will be apparent to those skilled in the art to which the invention pertains.

In the following example, efforts have been made to insure accuracy with respect to numbers used (e.g., amounts, temperature, etc.) but some experimental error and deviation should be accounted for. Unless indicated otherwise, temperature is in degrees C and pressure is at or near atmospheric.

EXAMPLE 1

1,3,5-Tris-O-acyl-2-deoxy-D-ribofuranose was readily synthesized by treating commercially available 2-deoxy-D-ribofuranose with a large excess of acetic anhydride or benzoyl chloride in pyridine. Both 1,3,5-O-trisacetyl- and trisbenzoyl-2-deoxy-D-ribofuranose could be recrystallized from ethanol. The acetyl derivative was mainly the alpha-isomer, and the benzoyl derivative gave the two isomers in 1/1 ratio. No pyranoside derivative was formed (less than 5%). 1,3,5-O-tris(TBDMS)-2'-deoxy-D-ribofuranoside was synthesized from deoxyribose by reaction with t-butyldimethylsilyl chloride/imidazole/DMF.

The anomeric acetal was readily exchanged with an alcohol in the presence of an acid catalyst, such as $ZnBr_2$, to give the alcohol derivative of either 3,5-O-diacyl- or 3,5-O-di-TBDMS-2'-deoxy-ribofuranose. Removal of the 3,5-O-protecting groups with base (methanol/1M $K_2CO_3$ for acyl) or fluoride ions (1M tetrabutylammonium fluoride in THF for TBDMS) gave the substituted 2'-deoxy-ribofuranose derivatives.

Alcohols containing various functionalities have been incorporated this way. Representative examples are 4-methyloxycarbonylbenzyl, 4-nitrophenethyl, TFA-NH-alkyl(aryl), and N-(4-nitrobenzyloxycarbonyl)/FMOC- 6-aminohexyl. They were all prepared directly from the correponding alcohol and 1,3,5-tri-O-acyl-2'-deoxy-D-ribofuranose.

Preparation of S-trityl-11-mercapto-1-undecyl was achieved via the 11-bromo-1-undecyl derivative. After preparation of the 11-bromo-1-undecyl 3,5-di-O-acetyl-2-deoxy-D-ribofuranose reaction with tritylmercaptane (Tr-SH) in the presence of base (one equivalent of aq. NaOH) afforded S-trityl-11-mercaptoundecyl 2-deoxy-D-ribofuranose. Alternatively, S-Tr-11-mercapto-1-undecanol could be prepared and used as the alcohol component. Alternatively, it is possible to incorporate alcohols containing a disulfite, —S—S—. The O-levulinyl-11-oxo-undecyl derivative was prepared via the 11-bromo derivative. After removal of the acetyl groups, displacement of bromine with the Cs-salt of levulinic acid afforded O-levulinyl-11-oxy-undecyl 2-deoxy-D-ribofuranose. Alternatively, preformed O-levulinyl-11-oxy-1-undecanol could be used as the alcohol component.

The appropriate alkyl 2-deoxy-D-ribofuranoside analogs were converted to the 5-DMT derivatives using standard literature procedures. The two anomeric stereoisomers gave rise to DMT species with quite different mobilities during silica gel chromatography. All DMT intermediates were purified by silica gel chromatography, and the two anomeric stereoisomers were readily separated. The various DMT intermediates were converted to the 3-O-N,N-diisopropyl-cyanoethyl-phosphoramidites using standard literature procedures, and they could be used like normal nucleoside cyanoethylphosphoramidites during automated oligonucleotide synthesis.

Removal of protecting groups from chemically synthesized oligonucleotides required only minimal changes to the standard procedures.

4-methyloxycarbonylbenzyl 2-deoxy-D-ribofuranose: Hydrolysis of methyl ester and succinate linkage to support was carried out with water/TEA/dioxane (1:1:10 v/v; 18 hours) prior to exposure to ammonium hydroxide.

TFA/FMOC-NH-alkyl required only standard deprotection with ammonium hydroxide. For 4-nitrophenethyl and N-(4-nitrobenzyloxy-carbonyl)-6-aminohexyl: reduction of the nitro group to an anilino group was conducted with 0.1M sodium dithionite/1M TEAB/dioxane for 5 hours, washed, and then deprotected with ammonium hydroxide to give the free anilino- and amino derivatized oligomer, respectively, which was purified by PAGE.

On support treatment with HPAA reagent, the DNA synthesis can be continued on the same support to produce branched oligomers. With proper choice of side-arm length, the monomer is useful for making 3'-3' linked oligodeoxynucleotides for cross-over triple helix formation. An example is O-levulinyl-2-oxyethyl 5-DMT-O-2-deoxy-D-ribofuranoside 3'-O-succ-CPG; the first strand is synthesized using 5'-DMT, capped, the levulinyl group removed and synthesis continued at the 2-hydroxyethyl side-chain. Deprotection gives the desired 5'-$DNA_1$-3'3'-$DNA_2$-5' oligomer.

We claim:

1. A polynucleotide reagent having the structural formula:

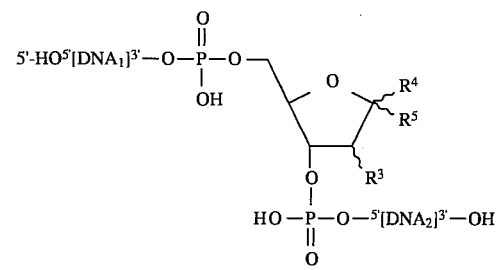

wherein:

$DNA_1$ is a first segment of DNA;

$DNA_2$ is a second segment of DNA;

$R^3$ is selected from the group consisting of hydrogen, hydroxyl, sulfhydryl, halogeno, amino, alkyl, allyl, —$OR^6$ wherein $R^6$ is alkyl, allyl, silyl or phosphate;

$R^4$ is either hydrogen or —$(CH_2)_m OR^7$ wherein $R^7$ is alkyl or —$(CO)R^8$, $R^8$ is alkyl, and m is an integer in the range of 0 to 12 inclusive;

$R^5$ is —A—Z—$X(R^9)_n$;

A is oxygen, sulfur or methylene;

Z is arylene, $C_6$-$C_{18}$ aralkylene or $C_1$-$C_{12}$ alkylene containing 0 to 6 heteroatoms selected from the group consisting of O, S, N, Si and Se and 0 to 6 linkages selected from the group consisting of —CO—, —COO—, —CONH—, —NHCO—, —S—S—, —$SO_2$—, —CH(OH)—CH(OH)—, —CH($OR^{15}$)—

CH(OR$^{15}$)—, —O—PO(O$^-$)—O—,
—O—PO(R$^{15}$)—, —O—PO(OR$^{15}$)—O—,
—O—PO(OR$^{15}$)—R$^{16}$— and —PO(OR$^{15}$)—O—R$^{16}$— in which R$^{15}$ is lower alkyl and R$^{16}$ is lower alkylene, and, if Z is aralkylene or alkylene, containing 0 to 3 unsaturated bonds;

X is selected from the group consisting of —NH—, —CONH—, —NHCO—, —CO—, —S— and —Si≡;

R$^9$ is hydrogen, a protecting group, or a detectable label; and n is 1 when X is —NH—, —CONH—, —NHCO—, —CO—, or —S—, and is 3 when X is —Si≡.

2. A polynucleotide reagent having the structural formula

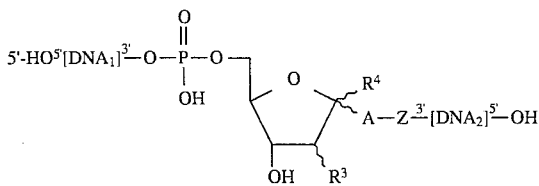

wherein:

DNA$_1$ is a first segment of DNA;

DNA$_2$ is a second segment of DNA;

R$^3$ is selected from the group consisting of hydrogen, hydroxyl, sulfhydryl, halogeno, amino, alkyl, allyl, —OR$^6$ wherein R$^6$ is alkyl, allyl, silyl or phosphate;

R$^4$ is either hydrogen or —(CH$_2$)$_m$OR$^7$ wherein R$^7$ is alkyl or —(CO)R$^8$, R$^8$ is alkyl and m is an integer in the range of 0 to 12 inclusive;

A is oxygen, sulfur or methylene; and

Z is arylene, C$_6$–C$_{18}$ aralkylene or C$_1$–C$_{12}$ alkylene containing 0 to 6 heteroatoms selected from the group consisting of O, S, N, Si and Se and 0 to 6 linkages selected from the group consisting of —CO—, —COO—, —CONH—, —NHCO—, —S—S—, —SO$_2$—, —CH(OH)—CH(OH)—, —CH(OR$^{15}$)—CH(OR$^{15}$)—, —O—PO(O$^-$)—O—, —O—PO(R$^{15}$)—, —O—PO(OR$^{15}$)—O—, —O—PO(OR$^{15}$)—R$^{16}$— and —PO(OR$^{15}$)—O—R$^{16}$— in which R$^{15}$ is lower alkyl and R$^{16}$ is lower alkylene, and, if Z is aralkylene or alkylene, containing 0 to 3 unsaturated bonds.

3. A polynucleotide reagent having the structural formula

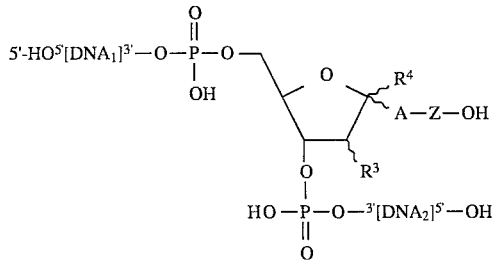

wherein:

DNA$_1$ is a first segment of DNA;

DNA$_2$ is a second segment of DNA;

R$^3$ is selected from the group consisting of hydrogen, hydroxyl, sulfhydryl, halogeno, amino, alkyl, allyl, —OR$^6$ wherein R$^6$ is alkyl, allyl, silyl or phosphate;

R$^4$ is either hydrogen or —(CH$_2$)$_m$OR$^7$ wherein R$^7$ is alkyl or —(CO)R$^8$, R$^8$ is alkyl and m is an integer in the range of 0 to 12 inclusive;

A is oxygen, sulfur or methylene; and

Z is arylene, C$_6$–C$_{18}$ aralkylene or C$_1$–C$_{12}$ alkylene containing 0 to 6 heteroatoms selected from the group consisting of O, S, N, Si and Se and 0 to 6 linkages selected from the group consisting of —CO—, —COO—, —CONH—, —NHCO—, —S—S—, —SO$_2$—, —CH(OH)—CH(OH)—, —CH(OR$^{15}$)—CH(OR$^{15}$)—, —O—PO(O$^-$)—O—, —O—PO(R$^{15}$)—, —O—PO(OR$^{15}$)—O—, —O—PO(OR$^{15}$)—R$^{16}$— and —PO(OR$^{15}$)—O—R$^{16}$— in which R$^{15}$ is lower alkyl and R$^{16}$ is lower alkylene, and, if Z is aralkylene or alkylene, containing 0 to 3 unsaturated bonds.

4. A branched polynucleotide reagent having the structural formula

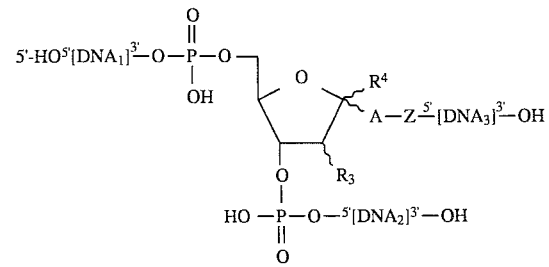

wherein:

DNA$_1$ is a first segment of DNA;

DNA$_2$ is a second segment of DNA;

DNA$_3$ is a third segment of DNA;

R$^3$ is selected from the group consisting of hydrogen, hydroxyl, sulfhydryl, halogeno, amino, alkyl, allyl, —OR$^6$ wherein R$^6$ is alkyl, allyl, silyl or phosphate;

R$^4$ is either hydrogen or —(CH$_2$)$_m$OR$^7$ wherein R$^7$ is alkyl or —(CO)R$^8$, R$^8$ is alkyl, and m is an integer in the range of 0 to 12 inclusive;

A is oxygen, sulfur or methylene; and

Z is arylene, C$_6$–C$_{18}$ aralkylene or C$_1$–C$_{12}$ alkylene containing 0 to 6 heteroatoms selected from the group consisting of O, S, N, Si and Se and 0 to 6 linkages selected from the group consisting of —CO—, —COO—, —CONH—, —NHCO—, —S—S—, —SO$_2$—, —CH(OH)—CH(OH)—, —CH(OR$^{15}$)—CH(OR$^{15}$)—, —O—PO(O$^-$)—O—, —O—PO(R$^{15}$)—, —O—PO(OR$^{15}$)—O—, —O—PO(OR$^{15}$)—R$^{16}$— and —PO(OR$^{15}$)—O—R$^{16}$— in which R$^{15}$ is lower alkyl and R$^{16}$ is lower alkylene, and, if Z is aralkylene or alkylene, containing 0 to 3 unsaturated bonds.

5. In a method for making a polynucleotide reagent comprising sequentially coupling nucleotidic monomers to a growing oligonucleotide chain, the improvement which comprises introducing an abasic site into the polynucleotide reagent by replacing a fraction of the nucleotidic monomers with the reagent of claim 4.

\* \* \* \* \*